United States Patent [19]

Righton

[11] Patent Number: 5,801,134
[45] Date of Patent: Sep. 1, 1998

[54] CLEANSING PRODUCT

[75] Inventor: Abigail Righton, Nr. Chichester, England

[73] Assignee: The Body Shop International Plc, West Sussex, England

[21] Appl. No.: 734,449

[22] Filed: Oct. 17, 1996

Related U.S. Application Data

[63] Continuation of Ser. No. 499,914, Jul. 11, 1995, abandoned.

[30] Foreign Application Priority Data

Jul. 12, 1994 [GB] United Kingdom ............... 9413981

[51] Int. Cl.$^6$ ...................... C11D 17/00; A61K 7/50
[52] U.S. Cl. ............... 510/130; 510/139; 510/141; 510/145; 510/151; 510/156; 510/462; 510/463; 510/466; 510/473; 510/475; 424/400
[58] Field of Search ............... 510/130, 139, 510/141, 151, 155, 156, 145, 462, 463, 466, 473, 475; 424/400

[56] References Cited

U.S. PATENT DOCUMENTS

| | | | |
|---|---|---|---|
| 2,356,903 | 8/1944 | Wood | 510/156 |
| 2,560,097 | 7/1951 | Emerson, Jr. et al. | 510/156 |
| 2,845,391 | 7/1958 | Searle | 510/156 |
| 3,129,187 | 4/1964 | Meehan | 510/156 |
| 3,248,333 | 4/1966 | O'Roark | 510/156 |
| 3,689,437 | 9/1972 | McLaughlin | 252/557 |
| 4,100,097 | 7/1978 | O'Roark | 510/156 |
| 4,151,105 | 4/1979 | O'Roark | 252/145 |
| 4,424,234 | 1/1984 | Alderson et al. | 424/317 |
| 4,941,990 | 7/1990 | McLaughlin | 510/151 |
| 4,976,953 | 12/1990 | Orr et al. | 424/47 |
| 5,013,473 | 5/1991 | Norbury et al. | 252/174.13 |
| 5,171,151 | 12/1992 | Barthold | 434/82 |
| 5,182,103 | 1/1993 | Nakane et al. | 424/78.03 |
| 5,227,086 | 7/1993 | Kacher et al. | 252/112 |
| 5,262,079 | 11/1993 | Kacher et al. | 252/112 |
| 5,264,144 | 11/1993 | Moroney et al. | 252/117 |
| 5,264,145 | 11/1993 | French et al. | 252/117 |
| 5,385,685 | 1/1995 | Humphreys et al. | 252/174.17 |
| 5,389,279 | 2/1995 | Au et al. | 252/108 |
| 5,425,892 | 6/1995 | Taneri et al. | 252/134 |

FOREIGN PATENT DOCUMENTS

| | | |
|---|---|---|
| 0370969 | 5/1990 | European Pat. Off. . |
| 5 3053-438 | 5/1978 | Japan . |
| 678063 | 7/1991 | Switzerland . |

*Primary Examiner*—Douglas J. McGinty
*Assistant Examiner*—Lorna M. Douyon
*Attorney, Agent, or Firm*—Banner & Witcoff, Ltd.

[57] ABSTRACT

A solid malleable non-hardenable cleansing product for personal use having a plasticine like consistency comprising 35% to 80% by weight of powder material, such as Kaolin, 10% to 25% by weight of surfactant material and 5% to 28% by weight of anhydrous base material to give a pH neutral, vegetarian, soap-free product.

4 Claims, No Drawings

CLEANSING PRODUCT

This application is a continuation of application Ser. No. 08/499,914, filed Jul. 11, 1995 now abandoned.

This invention relates to a cleansing product for personal use.

It is known to provide cleansing products for personal use, usually referred to as soaps, in either the form of a solid cake or in the form of a liquid or gel.

Attempts have been made to form kneadable cleansing products. One known form of kneadable soap is based on a gelatin matrix made malleable by the addition of paraffin or mineral oils. Such a product is, however, not suitable for many applications, being neither vegetarian not free of mineral oils, and harsh on delicate skins. Further malleable soaps have been made which remedy this harshness but these cleansing agents must be kept moist to remain malleable.

The present invention seeks to provide an alternative form of non-hardenable malleable cleansing product, or soap, which is attractive to young children.

According to the present invention there is provided a cleansing product for personal use( in the form of a solid composition with a plastic consistency, the composition comprising 35% to 80% by weight of powder material, 10% to 25% by weight of surfactant material and 5% to 28% by weight of anhydrous base material.

The powder material preferably consists of one or more of natural or synthetic hydrated aluminium silicate, metallic oxides, magnesium silicate, silicate minerals, vegetable starches, plant fines, synthetic polymer powders, calcium carbonate, cellulose and cellulose derivatives. The surfactant material preferably consists of one or more of an anionic, nonionic or amphoteric surfactant. The anhydrous base material may comprise one or more of plant oils/waxes/butters; synthetic waxes/butters, hydrogenated oils, fatty esters, fatty alcohols, sorbitol esters, lanolin, lanolin derivatives, silicone waxes, silicone oils, silicone copolymers.

The product may further contain one or more of the following:- water, dyestuff, pigments, UV absorbers, antioxidants, fragrance, preservatives, humectants, vitamins, plant extracts, glycols, skin conditioning agent and bittering additives.

A preferred composition for the cleansing product is approximately 60% by weight of Kaolin, 20% by weight of Sodium Laureth Sulphate, 15% to 19% of an anhydrous base material comprising a texturiser in the form of Vegetable Starch and Bis-Diglyceryl Fatty Ester Adipate and small percentages of preservatives, colourants and fragrance. Preferably, the Kaolin, Vegetable Starch, and some at least of the preservatives and pigments are in powder form.

A preferred method of manufacture comprises the following steps:

1. The dye solutions are diluted by dissolving in water in an approximate ratio of 5 parts of dye solution to 100 parts of water.
2. The dye solutions are then combined with the cleansing agent, Sodium Laureth Sulphate to form a surfactant phase.
3. The powder ingredients, that is, the Vegetable Starch, which has been already subjected to a sieving operation, the Kaolin, the powder preservatives and pigments are then blended in a powder mixer/blender until a homogenous powder phase is formed.
4. The texturiser in the form of the Bis-Diglyceryl Fatty Ester Adipate is separately melted and, whilst in the molten phase, fragrance and further preservatives are added, the mix being blended by stirring, to form a molten phase.

The surfactant phase and the molten phase are added to the homogenous powder in a blending machine and the composition is mixed until the batch is homogenous and the desired plastic, mouldable, texture is fully formed.

The bulk material is then extruded or moulded into a final desired shape prior to packaging and labelling.

In a modified method of manufacture for the product, the powder materials comprising Kaolin, Vegetable Powder, preservatives and pigments are mixed with dispersion to form a powder phase which is homogenous, smooth and uniform.

Dye solutions are prepared by dissolving dye in water in an approximate ratio of 5 to 100 parts by weight in liquid form and are then added to the powder phase. Mixing is continued until the combined ingredients are completely uniform and homogenous.

Texturiser in the form of Bis-Diglyceryl Fatty Ester Adipate is separately melted by heating to a temperature of 55° C. to 60° C. to form a molten phase.

The molten phase and the surfactant/cleansing agent which is in the form of an aqueous paste, are then mixed with the mix of the powder phase and the dyes without dispersion until a dough-like or plasticine-like texture forms and the bulk material is smooth, uniform and homogenous.

The finished bulk is then extruded and/or moulded into the desired shape ready for packaging and labelling.

Products formed in accordance with the present invention and which may be manufactured by the above processes have the following advantages:

1. can be used when wetted or dry for polymorphic modelling;
2. can be used for topical body cleansing when wetted, during which application a lather or foam is produced;
3. is suitable for vegetarians;
4. is soap-free and petrolatum free
5. has a pH close to neutral(7.0–7.5) in contrast to conventional soaps which have a high pH (>9.0).

I claim:

1. A cleansing product for personal use in the form of a solid composition with a dough-like plastic consistency, wherein the composition is malleable whether or not the product is wetted, is suitable for vegetarians and contains no gelatin, paraffin, or mineral oils, is soap-free and comprises 35% to 80% by weight of powder material, 10% to 25% by weight of surfactant material and 5% to 28% by weight of anhydrous base material, wherein the powder material is selected from the group consisting of natural or synthetic hydrated aluminum silicate, metallic oxides, magnesium silicate, silicate minerals, vegetable starches, plant fines, synthetic polymer powders, calcium carbonate, cellulose, and cellulose derivatives, the surfactant material is selected from the group consisting of anionic, nonionic, and amphoteric surfactants, and the anhydrous base material is selected from the group consisting of plant oils, plant waxes, plant butters, synthetic waxes, synthetic butters, hydrogenated oils, fatty esters, fatty alcohols, sorbitol esters, lanolin, lanolin derivatives, silicone waxes, silicone oils, and silicone copolymers.

2. A cleansing product according to claim 1, wherein the product further includes at least one of the following: water, dyestuff, pigments, UV absorbers, antioxidants, fragrance, preservatives, humectants, vitamins, plant extracts, glycols, skin conditioning agent and bittering additives.

3. A cleansing product for personal use in the form of a solid composition with a plastic consistency, wherein the composition is soap-free and comprises 60% by weight of Kaolin, 20% by weight of sodium laureth sulfate, 15% to 19% by weight of texturizer comprising vegetable starch and bis-diglyceryl fatty ester adipate and the balance including preservatives, pigments and fragrance.

4. A cleansing product according to claim 3, wherein the Kaolin, vegetable starch, and at least one of the preservatives and pigments are in powder form.

* * * * *